(12) United States Patent
Carmody et al.

(10) Patent No.: US 10,682,109 B2
(45) Date of Patent: Jun. 16, 2020

(54) CHECK VALVE ASSEMBLY

(71) Applicant: Illinois Tool Works Inc., Glenview, IL (US)

(72) Inventors: Colm M. Carmody, Listowel (IE); Gerard G. Henn, Limerick (IE); Robert R. Schaser, Chicago, IL (US); Raymond Jozwik, Hendersonville, TN (US)

(73) Assignee: Illinois Tool Works Inc., Glenview, IL (US)

( * ) Notice: Subject to any disclaimer, the term of this patent is extended or adjusted under 35 U.S.C. 154(b) by 116 days.

(21) Appl. No.: 15/762,639

(22) PCT Filed: Aug. 26, 2016

(86) PCT No.: PCT/US2016/048839
§ 371 (c)(1),
(2) Date: Mar. 23, 2018

(87) PCT Pub. No.: WO2017/062110
PCT Pub. Date: Apr. 13, 2017

(65) Prior Publication Data
US 2018/0296175 A1  Oct. 18, 2018

Related U.S. Application Data

(60) Provisional application No. 62/238,203, filed on Oct. 7, 2015.

(51) Int. Cl.
*A61B 6/00* (2006.01)
*A61M 39/24* (2006.01)
(Continued)

(52) U.S. Cl.
CPC .............. *A61B 6/481* (2013.01); *A61B 6/032* (2013.01); *A61M 5/007* (2013.01); *A61M 5/19* (2013.01);
(Continued)

(58) Field of Classification Search
CPC ......... Y10T 137/7838; Y10T 137/7879; Y10T 137/789; A61B 6/481; A61B 6/032;
(Continued)

(56) References Cited

U.S. PATENT DOCUMENTS 3,297,048 A * 1/1967 Imhof .................. B60T 11/323
137/512
3,807,445 A * 4/1974 McPhee ............ A61M 16/0051
137/557
(Continued)

FOREIGN PATENT DOCUMENTS

| CN | 1997553 | 7/2007 |
|---|---|---|
| CN | 102046220 | 5/2011 |

(Continued)

OTHER PUBLICATIONS

International Search Report and Written Opinion for PCT/US2016/048839.

*Primary Examiner* — Marina A Tietjen
*Assistant Examiner* — Frederick D Soski
(74) *Attorney, Agent, or Firm* — The Small Patent Law Group LLC; Joseph M. Butscher (57) ABSTRACT

A check valve assembly is configured to couple to a first container that retains a first fluid and a second container that retains a second fluid. The check valve includes a fluid inlet housing including a first fluid inlet port defining a first fluid inlet channel, and a second fluid inlet port defining a second fluid inlet channel. A fluid outlet housing is coupled to the fluid inlet housing. The fluid outlet housing includes a fluid (Continued)

outlet port defining a fluid outlet channel. A first diaphragm is seated over the first fluid inlet channel. At least a portion of the first diaphragm is configured to unseat over the first fluid inlet channel to allow the first fluid to pass from the first fluid inlet channel into the fluid outlet channel. A second diaphragm is seated over the second fluid inlet channel. At least a portion of the second diaphragm is configured to unseat over the first fluid inlet channel to allow the second fluid to pass from the second fluid inlet channel into the fluid outlet channel.

20 Claims, 5 Drawing Sheets (51) Int. Cl.
*A61B 6/03* (2006.01)
*A61M 5/00* (2006.01)
*A61M 5/19* (2006.01)
*F16K 15/14* (2006.01)
*A61M 39/10* (2006.01)
*A61M 5/178* (2006.01)

(52) U.S. Cl.
CPC ............ A61M 39/24 (2013.01); F16K 15/141 (2013.01); *A61M 2005/1787* (2013.01); *A61M 2039/1083* (2013.01); *A61M 2039/1088* (2013.01); *A61M 2039/246* (2013.01); *A61M 2039/2446* (2013.01); *A61M 2039/2453* (2013.01); *A61M 2039/2466* (2013.01)

(58) Field of Classification Search
CPC ........ A61M 5/007; A61M 5/19; A61M 39/24; A61M 2005/1787; A61M 2039/2453; F16K 15/141
See application file for complete search history.

(56) References Cited

U.S. PATENT DOCUMENTS

| | | | | |
|---|---|---|---|---|
| 4,222,407 A * | 9/1980 | Ruschke | ............... | F16K 15/141 137/512.15 |
| 4,244,378 A * | 1/1981 | Brignola | ............ | A61B 5/15003 137/843 |
| 4,246,932 A | 1/1981 | Raines | | |
| 4,354,492 A * | 10/1982 | McPhee | .................. | A61M 5/40 137/528 |
| 4,415,003 A * | 11/1983 | Paradis | .................. | F16K 15/14 137/843 |
| 4,556,086 A * | 12/1985 | Raines | .................. | F16K 15/141 137/843 |
| 4,762,149 A * | 8/1988 | Pickl, Jr. | ............... | F16K 15/141 137/843 |
| 4,838,875 A * | 6/1989 | Somor | ...................... | A61J 1/10 604/247 |
| 4,946,448 A * | 8/1990 | Richmond | ............ | A61M 39/24 137/493.9 |
| 5,070,905 A * | 12/1991 | Paradis | .................. | A61M 39/04 137/606 |
| 5,190,067 A * | 3/1993 | Paradis | .................. | A61M 39/04 137/1 |
| 5,391,150 A * | 2/1995 | Richmond | ................ | A61J 1/10 604/111 |
| 5,431,185 A | 7/1995 | Shannon | | |
| 5,623,969 A * | 4/1997 | Raines | .................. | A61M 39/24 137/854 |
| 5,992,462 A * | 11/1999 | Atkinson | ............... | A61M 39/24 137/515.5 |
| 6,409,707 B1 * | 6/2002 | Guala | .................... | A61M 39/24 137/843 |
| 6,866,056 B1 * | 3/2005 | Scott | .................... | B60K 15/035 137/15.18 |
| 8,162,006 B2 * | 4/2012 | Guala | .................... | A61M 39/24 137/512.15 |
| 8,973,596 B2 * | 3/2015 | Hull | ..................... | F16K 15/023 137/1 |
| 10,286,202 B2 * | 5/2019 | Mosler | .................. | A61M 39/24 |
| 2002/0156431 A1 | 10/2002 | Feith | | |
| 2005/0121103 A1 | 6/2005 | Steigerwalt | | |
| 2005/0194047 A1 | 9/2005 | Bausmith | | |
| 2010/0300556 A1 * | 12/2010 | Carmody | ............... | A61M 39/24 137/528 |
| 2017/0281870 A1 * | 10/2017 | Kai | .................. | A61B 17/00491 |

FOREIGN PATENT DOCUMENTS

WO      WO 93/01859      2/1993
WO      WO 2014/140158      9/2014

* cited by examiner

FIG. 11

CHECK VALVE ASSEMBLY

RELATED APPLICATIONS

This application is a National Phase of International Application No. PCT/US2016/048839, filed Aug. 26, 2016, which relates to and claims priority benefits from U.S. Provisional Patent Application No. 62/238,203 entitled "Check Valve Assembly," filed Oct. 7, 2015, both of which are hereby incorporated by reference in their entireties.

FIELD OF EMBODIMENTS OF THE DISCLOSURE

Embodiments of the present disclosure generally relate to a check valve assembly, and, more particularly, to a check valve assembly that may be configured for medical applications, such as for use with computed tomography (CT) imaging.

BACKGROUND

During certain types of medical imaging (such as during computed tomography imaging), contrast agent may be used. For example, an individual may ingest or be injected with contrast agent before the imaging process. When the individual is being imaged, the contrast agent allows for more defined imaging results.

During an imaging session, saline and contrast merge within a connection joint that connects to a syringe through a conduit. A check valve is typically positioned within each of a saline line and a contrast line. For example, the saline line includes a first check valve, and the contrast line includes a separate and distinct second check valve. The check valves are separated from the connection joint. Because the check valves are separated from the connection joint, small amounts of contrast may be drawn into the saline during a flush through the connection joint (or vice versa), which may, in turn, affect the resulting acquired images of anatomy. For example, the contrast may form spots on a scanned image, thereby creating a false positive.

SUMMARY OF EMBODIMENTS OF THE DISCLOSURE

A need exists for a check valve assembly that prevents, minimizes, or otherwise reduces the possibility of saline and contrast undesirably mixing. A need exists for a check valve assembly that prevents, minimizes, or otherwise reduces the possibility of image false positives, such as may be caused by spots formed by contrast agent. A need exists for a simpler and more effective check valve assembly.

With those needs in mind, certain embodiments of the present disclosure provide a check valve assembly that is configured to couple to a first container that retains a first fluid and a second container that retains a second fluid. The check valve assembly includes a fluid inlet housing including a first fluid inlet port defining a first fluid inlet channel, and a second fluid inlet port defining a second fluid inlet channel. A fluid outlet housing is coupled to the fluid inlet housing. The fluid outlet housing includes a fluid outlet port defining a fluid outlet channel. A first diaphragm is seated over the first fluid inlet channel. At least a portion of the first diaphragm is configured to unseat over the first fluid inlet channel to allow the first fluid to pass from the first fluid inlet channel into the fluid outlet channel. A second diaphragm is seated over the second fluid inlet channel. At least a portion of the second diaphragm is configured to unseat over the second fluid inlet channel to allow the second fluid to pass from the second fluid inlet channel into the fluid outlet channel.

In at least one embodiment, each of the first and second diaphragms includes an annular edge radially extending from a central hub. The annular edge includes an outer rim that is thicker than the central hub.

The check valve assembly may include one or more walls surrounding a fluid chamber between the first and second fluid inlet channels and the fluid outlet channel. One or more guide ribs may inwardly extend from the wall(s). The guide ribs constrain, a least in part, one or both of the first and second diaphragms. The guide ribs are configured to guide fluid flow from the first and second inlet channels toward the fluid outlet channel. In at least one embodiment, each of the guide ribs includes a stem connected to a beveled tip.

The check valve assembly may include a deflecting barrier positioned between openings of the first and second fluid inlet channels.

The check valve assembly may include a first restraining protuberance that abuts into the first diaphragm, and a second restraining protuberance that abuts into the second diaphragm.

The check valve assembly may include a first plurality of supporting protuberances that control a range of deflection of the first diaphragm. The first plurality of supporting protuberances block further deflection of the portion(s) of the first diaphragm when the portion(s) of the first diaphragm unseats over the first fluid inlet channel. A second plurality of supporting protuberances control a range of deflection of the second diaphragm. The second plurality of supporting protuberances block further deflection of the portion(s) of the second diaphragm when the portion(s) of the second diaphragm unseats over the second fluid inlet channel.

Certain embodiments of the present disclosure provide a fluid delivery system that includes a first fluid container that retains a first fluid, a second fluid container that retains a second fluid, and a check valve assembly coupled to the first container and the second container. The check valve assembly includes a fluid inlet housing including a first fluid inlet port defining a first fluid inlet channel fluidly connected to the first fluid container, and a second fluid inlet port defining a second fluid inlet channel fluidly connected to the second fluid container. A fluid outlet housing is coupled to the fluid inlet housing. The fluid outlet housing includes a fluid outlet port defining a fluid outlet channel. A first diaphragm is seated over the first fluid inlet channel. At least a portion of the first diaphragm is configured to unseat over the first fluid inlet channel to allow the first fluid to pass from the first fluid inlet channel into the fluid outlet channel. A second diaphragm is seated over the second fluid inlet channel. At least a portion of the second diaphragm is configured to unseat over the second fluid inlet channel to allow the second fluid to pass from the second fluid inlet channel into the fluid outlet channel.

The fluid delivery system may also include a syringe fluidly connected to the fluid outlet port. In at least one embodiment, the first fluid container is a contrast container and the first fluid is a contrast agent, and the second fluid container is a saline container and the second fluid is saline.

Before the embodiments of the disclosure are explained in detail, it is to be understood that the disclosure is not limited in its application to the details of construction and the arrangement of the components set forth in the following description or illustrated in the drawings. The disclosure is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF EMBODIMENTS OF THE DISCLOSURE

Embodiments of the present disclosure provide a check valve assembly that is configured to prevent undesired mixing of contrast and saline, for example, during CT imaging or other medical procedures and/or imaging. The check valve assembly reduces the likelihood of false results.

Embodiments of the present disclosure provide a check valve assembly at the point where the contrast and saline merge, thereby preventing mixing when one fluid is being injected. Embodiments of the present disclosure lead to more accurate diagnoses and save costs (such as through a simpler and more efficient system and method).

Figure 1:
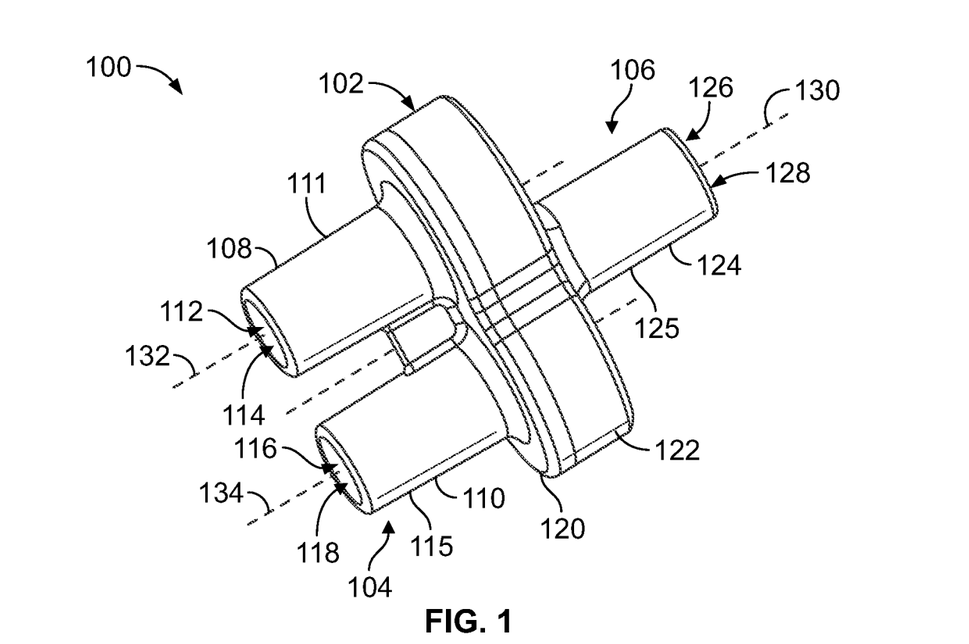
FIG. 1 illustrates a perspective view of a check valve assembly, according to an embodiment of the present disclosure.

FIG. 1 illustrates a perspective view of a check valve assembly 100, according to an embodiment of the present disclosure. The check valve assembly 100 may be a dual check valve assembly that is normally closed. The check valve assembly 100 includes a main body 102 that includes a fluid inlet (or entry) portion 104 coupled to a fluid outlet (or exit) portion 106. Each of the fluid inlet housing 104 and the fluid outlet housing 106 may be formed of a plastic, for example. The fluid inlet housing 104 may be securely connected to the fluid outlet housing 106, such as through ultrasonic welding. In at least one other embodiment, the fluid inlet housing 104 may be securely connected to the fluid outlet housing 106 through one or more adhesives, fasteners, bonding, and/or the like. In at least one other embodiment, the fluid inlet housing 104 and the fluid outlet housing 106 may be integrally molded and formed as a single piece, such as a unitary piece of injection-molded plastic.

The fluid inlet housing 104 includes a first fluid inlet port 108 and a second inlet port 110. The first fluid inlet port 108 includes an outer tubular wall 111 that defines a fluid inlet 112 that forms part of and leads into a fluid inlet channel 114. Similarly, the second fluid inlet port 110 includes an outer tubular wall 115 that defines a fluid inlet 116 that forms part of and leads into a fluid inlet channel 118.

The first and second fluid inlet ports 108 and 110 connect to a coupling base 120 that is coupled to a reciprocal coupling base 122 of the fluid outlet housing 106. The coupling base 122 connects to a fluid outlet port 124. The fluid outlet port 124 includes an outer tubular wall 125 that defines a fluid outlet 126 that forms part of and leads into a fluid outlet channel 128.

The fluid outlet port 124 includes a central longitudinal axis 130 that may be axially aligned with a central longitudinal axis of the check valve assembly 100. Central longitudinal axes 132 and 134 of the first fluid inlet port 108 and the second fluid inlet port 110, respectively, are offset from the central longitudinal axis 130 of the fluid outlet port 124. For example, the central longitudinal axis 132 is to one side of the central longitudinal axis 130, while the central longitudinal axis 134 is to an opposite side of the central longitudinal axis 130.

Figure 2:
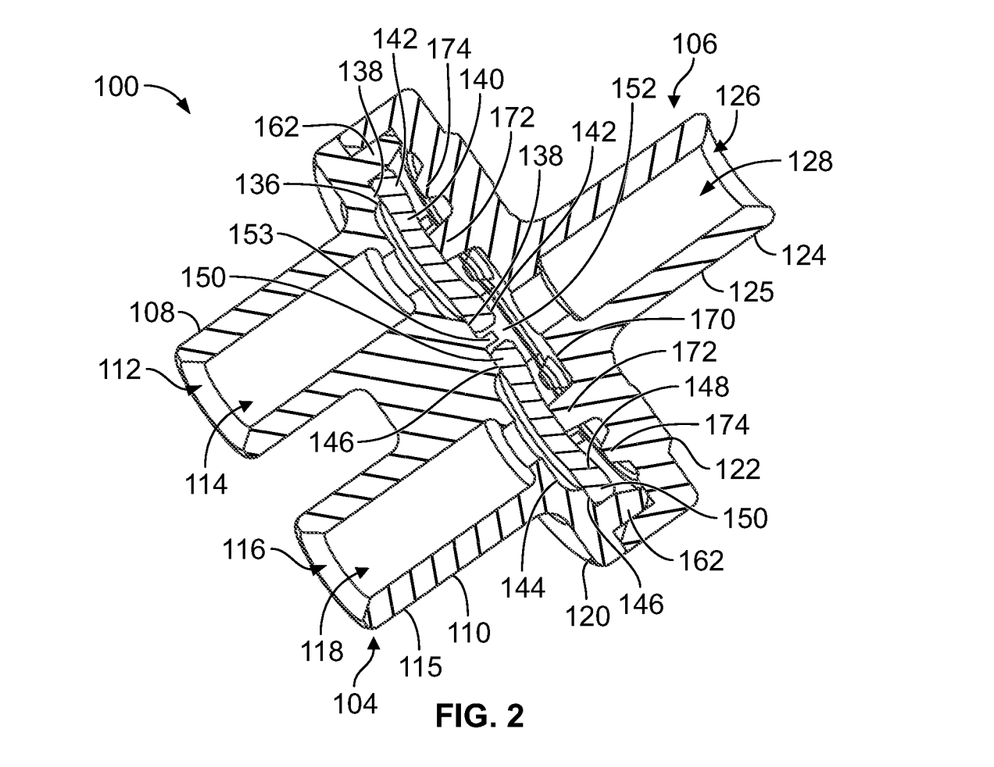
FIG. 2 illustrates a transverse cross-sectional view of a check valve assembly, according to an embodiment of the present disclosure.

FIG. 2 illustrates a transverse cross-sectional view of the check valve assembly 100. The fluid inlet channel 114 connects to a fluid opening 136 defined by an interior annular valve seat 138 of the coupling base 120. A first check valve in the form of a diaphragm 140 (which may be formed of rubber and disc shaped) extends over the fluid opening 136 in the closed position, such that an outer annular edge 142 seats on the valve seat 138. Similarly, the fluid inlet channel 118 connects to a fluid opening 144 defined by an interior annular valve seat 146 of the coupling base 120. A second check valve in the form of a diaphragm 148 (which may be formed of rubber and disc shaped) extends over the fluid opening 144 in the closed position, such that an outer annular edge 150 seats on the valve seat 146.

The fluid openings 136 and 144 connect to a central fluid chamber 152, which, in turn, connects to the fluid outlet channel 128. In operation, fluid passing through the fluid inlet channel 114 at sufficient fluid pressure causes the annular edge 142 to unseat from the valve seat 138. The fluid then passes from the fluid opening 136 into the central fluid chamber 152, and into the fluid outlet channel 128. Similarly, fluid passing through the fluid inlet channel 118 at sufficient fluid pressure causes the annular edge 150 to unseat from the valve seat 146. The fluid then passes from the fluid opening 144 into the central fluid chamber 152, and into the fluid outlet channel 128.

The diaphragms 140 and 148 prevent, minimize, or otherwise reduce the possibility of fluid within the fluid outlet channel 128 from passing back into the respective fluid openings 136 and 144. That is, to the extent that any fluid within the fluid outlet channel 128 tends to retreat back or back-flow towards the fluid openings 136 and/or 144, the back-flow pressure exerted into the diaphragms 140 and 148 increases the seating force of the diaphragms 140 and 148 into the respective valve seats 138 and 146, thereby preventing the fluid from passing into the fluid openings 136 and 144.

Figure 3:
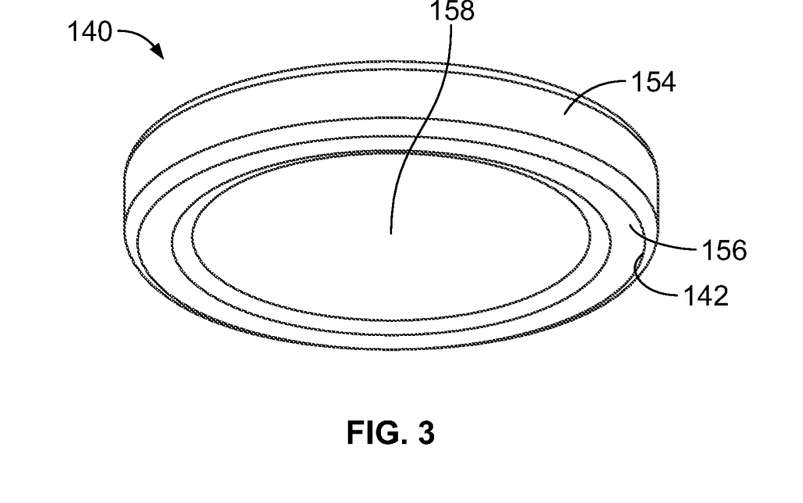
FIG. 3 illustrates a perspective bottom view of a diaphragm, according to an embodiment of the present disclosure.

FIG. 3 illustrates a perspective bottom view of the diaphragm 140, according to an embodiment of the present disclosure. While not shown in FIG. 3, the diaphragm 148 (shown in FIG. 2) may be constructed in the same manner as the diaphragm 140.

The diaphragm 140 includes an annular body 154 in which the outer annular edge 142 may include a raised or downwardly extending rim 156 that extends radially and below from a recessed central hub 158. Thus, the outer rim 156 is thicker than the central hub 158. While not shown in FIG. 3, the diaphragm 148 also includes an annular body in which an annular edge may include a raised or downwardly extending rim that extends below a recessed central hub. Referring to FIGS. 2 and 3, the raised rim 156 increases the contact area between the diaphragms 140, 148 and the respective valve seats 138 and 146, thereby providing increased, robust sealing therebetween.

Figure 4:
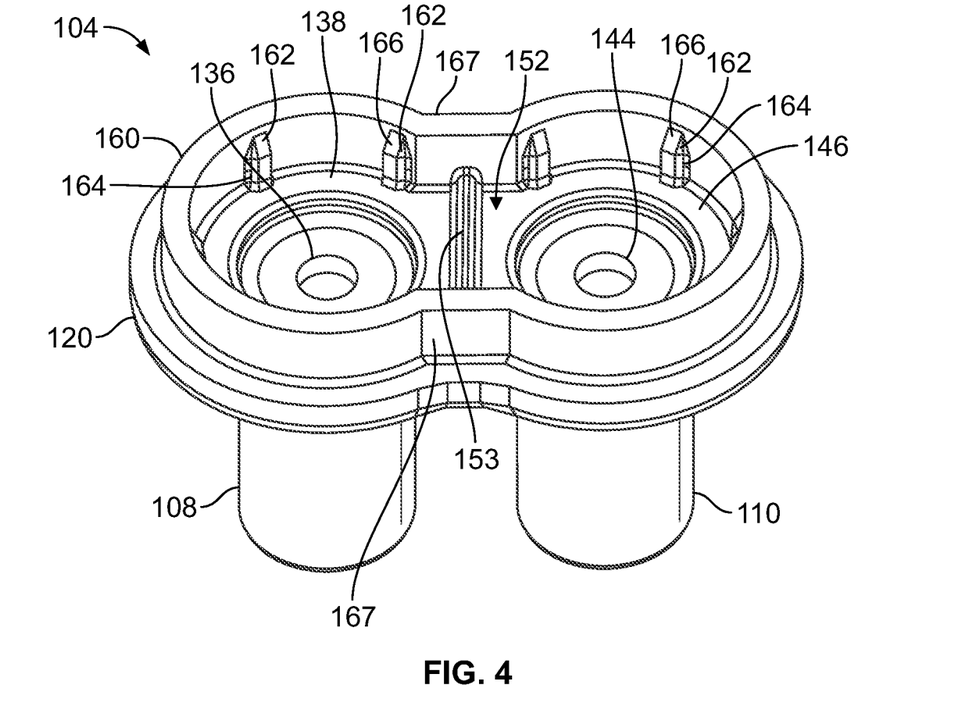
FIG. 4 illustrates a perspective top view of a fluid inlet housing, according to an embodiment of the present disclosure.

FIG. 4 illustrates a perspective top view of the fluid inlet housing 104, according to an embodiment of the present disclosure. The coupling base 120 includes an upstanding wall 160 surrounding the central fluid chamber 152. A plurality of guide ribs 162 inwardly extend from the wall 160 into the central fluid chamber 152. The guide ribs 162 may be regularly spaced about the wall 160. More or less guide ribs 162 than shown may be used.

Each of the diaphragms 140 and 148 (shown in FIG. 2) may be radially constrained (at least in part) between the guide ribs 162. Thus, the guide ribs 162 ensure that the diaphragms 140 and 148 are coaxially aligned over the respective fluid openings 136 and 144 and are configured to fully seat on the respective valve seats 138 and 146 in the closed positions.

Each of the guide ribs 162 includes a stem 164 extending upwardly from a valve seat 138 or 146. The stem 164 connects to a distal beveled tip 166. Referring to FIGS. 1 and 4, it has been found that the shape of the guide ribs 162 (including the stems 164 and the upper beveled tips 166) directs fluid flow up around the diaphragms 140 and 148 as the diaphragms 140 and 148 unseat from the valve seats 138 and 146.

As shown, a central deflecting barrier 153 (such as a rib, beam, wall, or other such barrier) may be disposed within the fluid chamber 152 between the fluid openings 136 and 144. The deflecting barrier 153 may span across the fluid chamber 152 between opposed wall segments 167. The deflecting barrier 153 deflects and redirects fluid flowing through the fluid opening 136 upwardly and away from the fluid opening 144, and vice versa. In this manner, the deflecting barrier 153 is configured to prevent undesired fluid mixing. The deflecting barrier 153 provides a barrier between the fluid openings 136 and 144 that reduces the possibility of fluid passing between the fluid openings 136 and 144.

Figure 5:
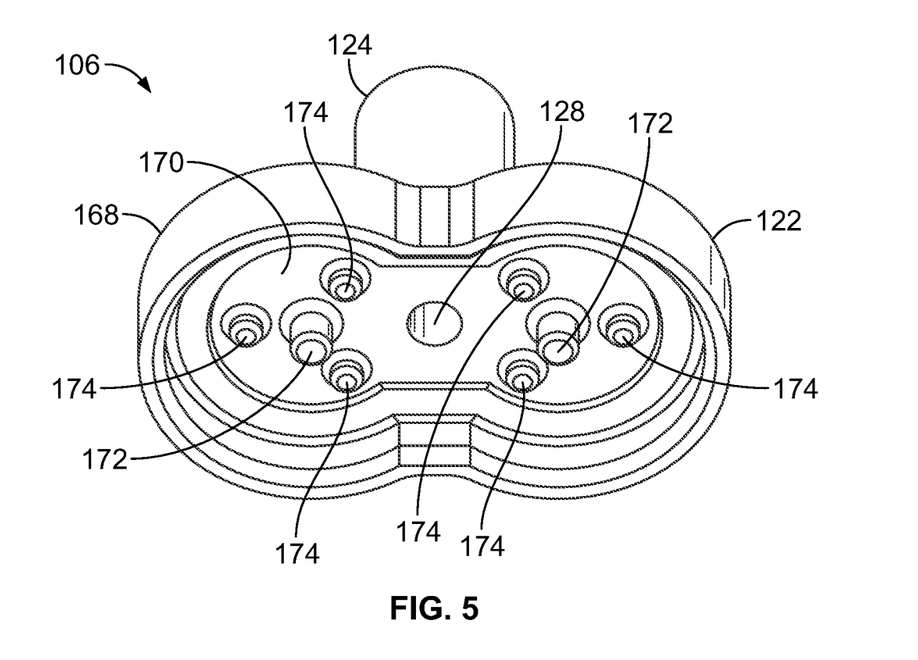
FIG. 5 illustrates a perspective bottom view of a fluid outlet housing, according to an embodiment of the present disclosure.

FIG. 5 illustrates a perspective bottom view of the fluid outlet housing 106, according to an embodiment of the present disclosure. The coupling base 122 includes an outer wall 168 surrounding a panel 170. Referring to FIGS. 2 and 5, a restraining protuberance 172 (for example, a central upstand such as such as a post, column, stud, nub, or the like) extends downwardly from the panel 170 above each of the diaphragms 140 and 148. The restraining protuberances 172 may be coaxially aligned with respective fluid inlet ports 108 and 110. The restraining protuberances 172 abut into centers of the diaphragms 140 and 148. In this manner, the restraining protuberances 172 maintain the diaphragms 140 and 148 over the fluid openings 136 and 144, whether the diaphragms 140 and 148 are in the closed or open positions.

A plurality of support protuberances 174 may extend downwardly from the panel 170. A plurality of support protuberances 174 (for example, upstands such as posts, columns, studs, nubs, or the like) may be positioned around each restraining protuberance 172. The support protuberances 174 may be regularly spaced around each restraining protuberance 172. More or less support protuberances 174 than shown may be used. In at least one embodiment, the fluid outlet housing 106 does not include any restraining protuberances 172.

The restraining protuberances 172 extend downwardly from the panel 170 a greater distance than do the support protuberances 174. When the diaphragms 140 and 148 are fully seated on the valves seats 138 and 146, respectively, the support protuberances 174 do not abut into the diaphragms 140 and 148 (whereas the restraining protuberances 172 abut into the diaphragms 140 and 148). As the diaphragms 140 and 148 are forced by fluid pressure off the valve seats 138 and 146, the outer annular portions of the diaphragms 140 and 148 may upwardly deflect into the support protuberances 174. In this manner, the support protuberances 174 may be sized and shaped to control deflection of the diaphragms 140 and 148, such as to control a flow rate of fluid out of the fluid openings 136 and 144 and/or maintain the resilience of the diaphragms 140 and 148. The support protuberances 174 are configured to prevent, minimize, or otherwise reduce the possibility that the diaphragms 140 and 148 flex beyond their elastic limits when subjected to increased outwardly-flowing fluid pressures and flows.

Figure 6:
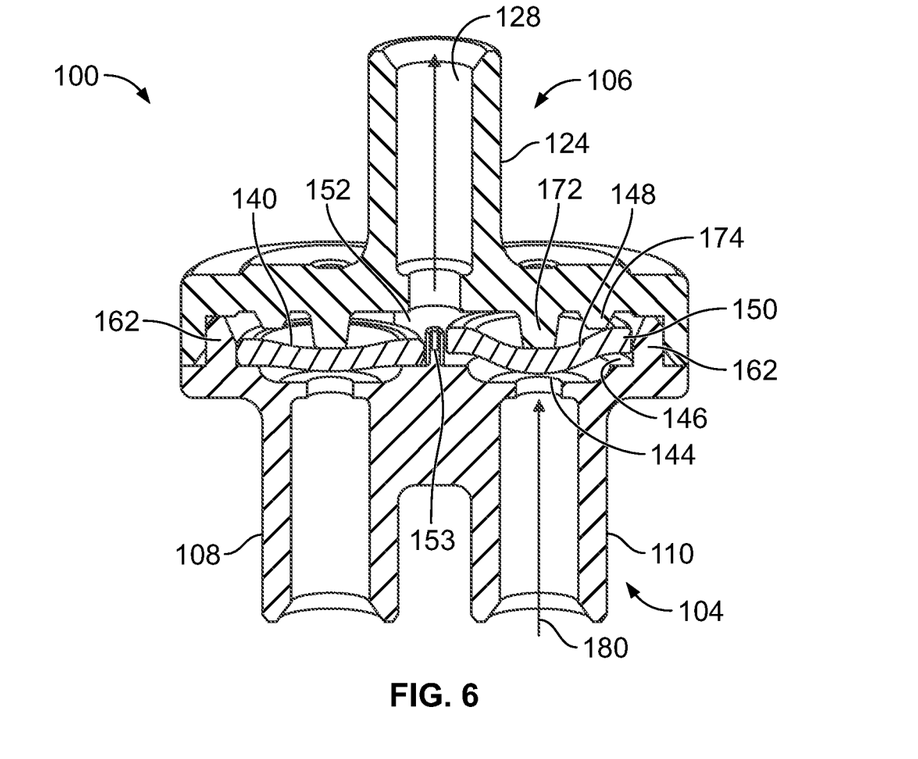
FIG. 6 illustrates a perspective cross-sectional view of a check valve assembly, according to an embodiment of the present disclosure.
Figure 7:
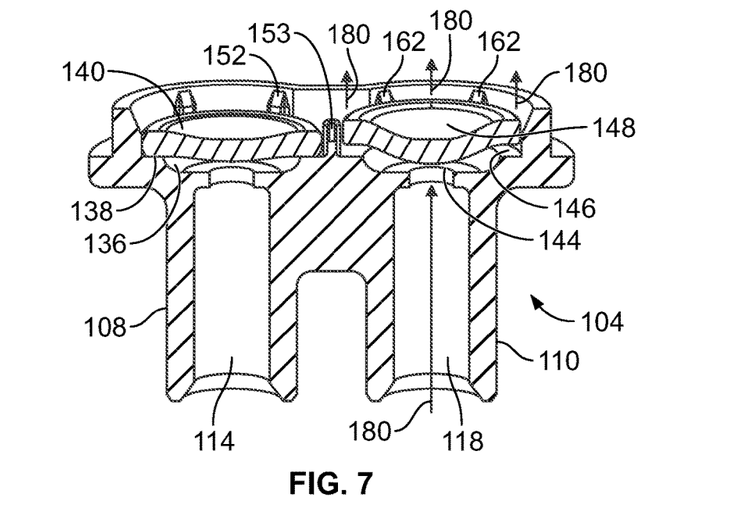
FIG. 7 illustrates a perspective cross-sectional view of a fluid inlet housing, according to an embodiment of the present disclosure.

FIG. 6 illustrates a perspective cross-sectional view of the check valve assembly 100. FIG. 7 illustrates a perspective cross-sectional view of the fluid inlet housing 104. Referring to FIGS. 6 and 7, fluid 180 is shown flowing into the fluid inlet channel 118 of the fluid inlet port 110. The fluid is of sufficient fluid pressure to unseat the annular edge 150 of the diaphragm 148 off the valve seat 144, thereby allowing the fluid 180 to flow around the annular edge 150 into the central fluid chamber 152 and into the fluid outlet channel 128. As shown, the restraining protuberance 172 abuts into a central portion (such as the central hub 158) of the diaphragm 148, thereby ensuring that the diaphragm remains centered over the fluid opening 144. The annular edge 150 may be forced into the support protuberances 174, which control the upward deflection of the diaphragm 148, as noted above.

Because fluid is not flowing through the fluid inlet channel 114, the diaphragm 140 remains seated on the valve seat 138. As such, the fluid 180 is unable to back-flow into the fluid inlet channel 114. The guide ribs 162 guide the flow of the fluid 180 into the fluid outlet channel 128.

When fluid flows through the fluid inlet channel 114 of sufficient force, operation of the diaphragms 140 and 148 is opposite than described above. That is, when fluid flows through fluid inlet channel 114, the diaphragm 140 unseats (thereby allowing fluid to flow around the diaphragm 140 and into the fluid outlet channel 128), while the diaphragm 148 remains seated (thereby preventing fluid from back-flowing into the fluid inlet channel 118).

When fluid pressure in either of the fluid inlet channels 114 or 118 rises above an opening threshold, the diaphragms 140 and 148 deflect away from the valve seats 138 and 146 open a fluid path to the fluid outlet channel 128. In at least one embodiment, the opening pressure specification range used in a CT set may be 1.5-6 pounds per square inch (psi). Optionally, the opening pressure may be adjusted by varying the thickness and/or shore hardness of the diaphragms 140 and 148, and/or the height of the restraining protuberance 172, which imparts pretension onto the diaphragms 140 and 148.

Fluid flow is uniformly directed to and around the outer periphery of the diaphragms 140 and 148 to minimize or otherwise reduce areas of restricted flow. The deflecting barrier 153 prevents flow from the active/open side of the check valve assembly 100 peeling open the diaphragm on the inactive/closed side. The deflecting barrier 153 is configured to deflect fluid flow, but does not cause a significant area of non-flow or dead space.

Figure 8:
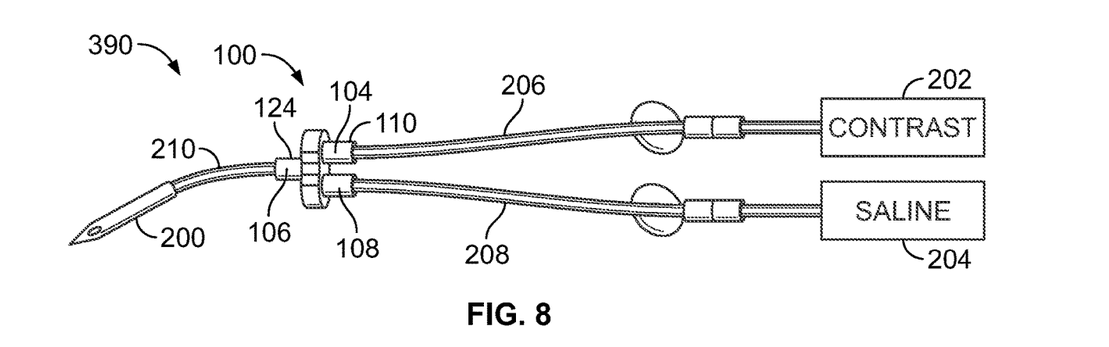
FIG. 8 illustrates a lateral view of a fluid delivery system, according to an embodiment of the present disclosure.

FIG. 8 illustrates a lateral view of a fluid delivery system 390, according to an embodiment of the present disclosure. The fluid delivery system 390 includes the check valve assembly 100 connecting a syringe 200 to a contrast agent container 202 and a saline container 204. The syringe 200 is configured to be inserted into anatomy (such as a vein) of an individual. The contrast agent container 202 contains liquid contrast agent. The saline container 204 includes liquid saline. Optionally, the containers 202 and 204 may contain different fluids.

Referring to FIGS. 1-8, the fluid inlet channel 118 of the fluid inlet port 110 is fluidly connected to the contrast container 202. The fluid inlet channel 114 of the fluid inlet port 108 is fluidly connected to the saline container 204. The fluid outlet channel 128 of the fluid outlet port 124 is fluidly connected to the syringe 200.

The contrast agent container 202 connects to the fluid inlet port 110 through a tube 206, while the saline container 204 connects to the fluid inlet port 108 through a tube 208. The syringe connects to the fluid outlet port 124 through a tube 210.

When contrast agent is delivered from the contrast agent container 202 at sufficient fluid pressure, the check valve assembly 100 allows the contrast agent to flow towards and into the syringe 200, while preventing the contrast agent from back-flowing into the fluid inlet port 108, as described above. Similarly, when saline is delivered from the saline container 204 at sufficient fluid pressure, the check valve assembly 100 allows the saline to flow towards and into the syringe 200, while preventing the saline from back-flowing into the fluid inlet port 110.

The check valve assembly 100 may be coupled to a Computed Tomography (CT) set (such as through solvent bonding). As such, the check valve assembly 100 provides a back check and an anti-siphon function. The check valve assembly 100 may replace two single check valves and a separate and distinct "Y" connector joint. The dual check assembly 100 integrates the two diaphragms 140 and 148 with respect to the respective fluid inlet channels 114 and 118, instead of positioning separate and distinct check valves in saline and contrast lines.

Figure 9:
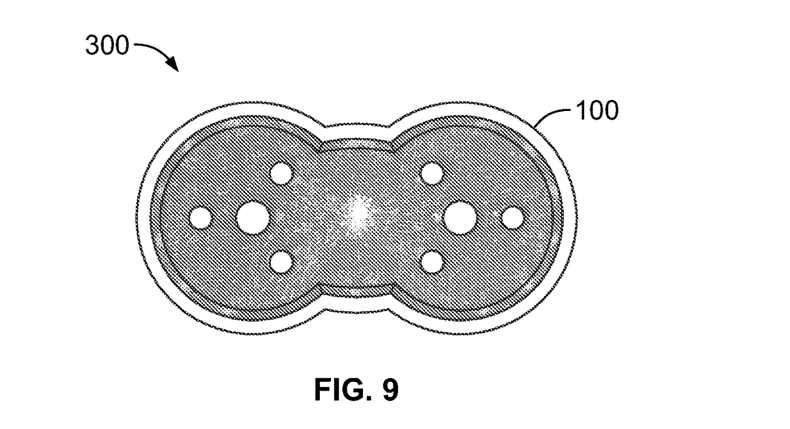
FIG. 9 illustrates a flow vector plot for a check valve assembly, according to an embodiment of the present disclosure.

FIG. 9 illustrates a flow vector plot 300 for the check valve assembly 100, according to an embodiment of the present disclosure. A Fluid Structure Interaction (FSI) simulation was conducted in which a number of different fluid exit geometries were considered. Based on the FSI, the geometry of the fluid outlet housing 106 (shown in FIG. 1, for example) provides efficient fluid flow, and ensures that areas of non-flow (or dead space) are minimized or otherwise reduced.

Figure 10:
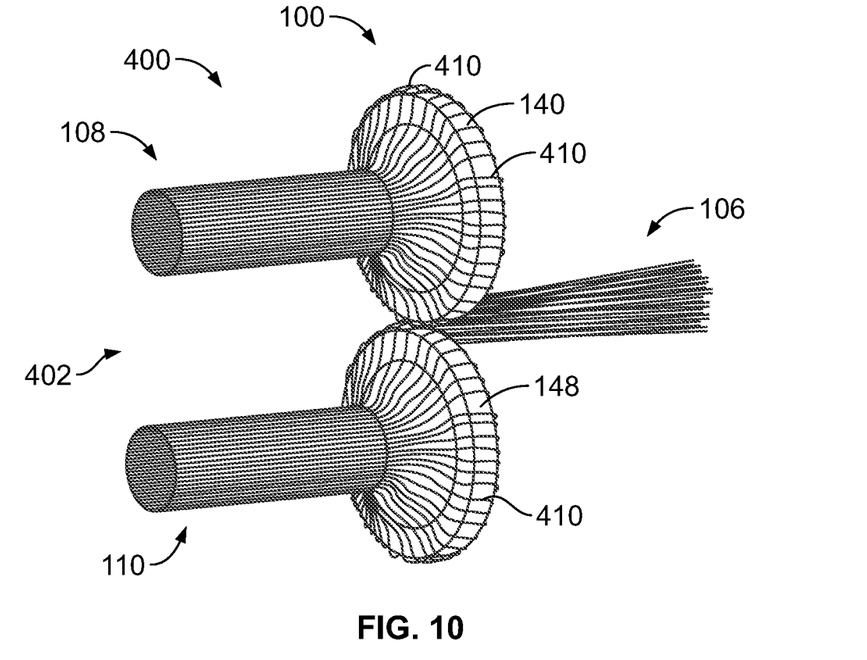
FIG. 10 illustrates a streamline plot from a fluid inlet side for flow through a check valve assembly with both fluid inlet ports open, according to an embodiment of the present disclosure.
Figure 11:
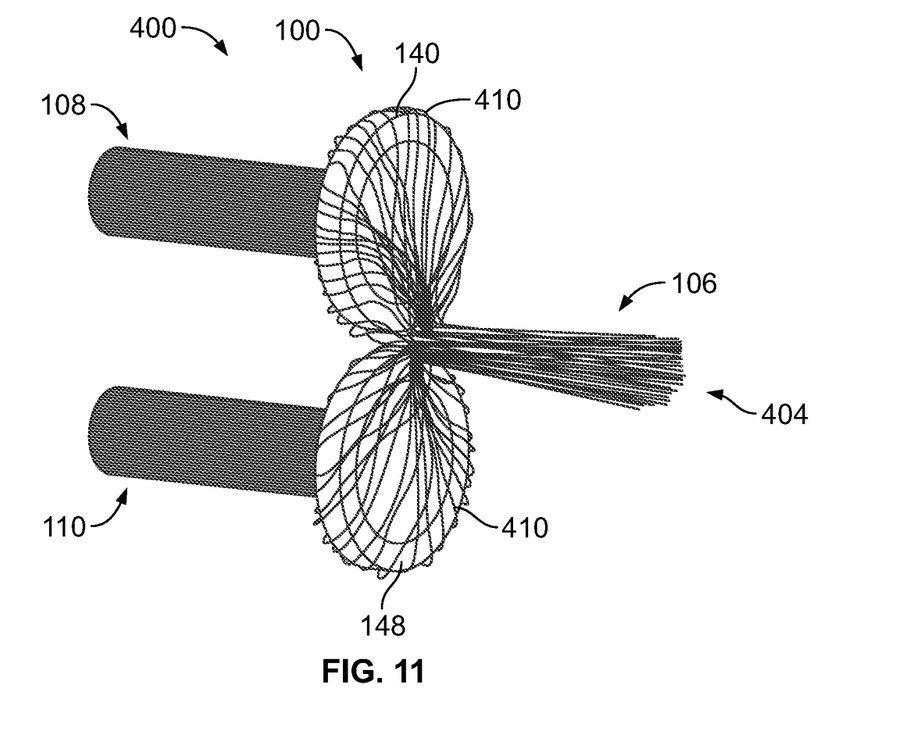
FIG. 11 illustrates a streamline plot from a fluid outlet side for flow through a check valve assembly with both fluid inlet ports open, according to an embodiment of the present disclosure.

FIG. 10 illustrates a streamline plot 400 from a fluid inlet side 402 for flow 410 through the check valve assembly 100 with both fluid inlet ports open 108 and 110, according to an embodiment of the present disclosure. FIG. 11 illustrates the streamline plot 400 from a fluid outlet side 404 for flow 410 through the check valve assembly 100 with both fluid inlet ports 108 and 110 open. As shown in FIGS. 10 and 11, fluid flow 410 is directed to the outer perimeters of the diaphragms 140 and 148, thereby eliminating, minimizing, or otherwise reducing areas of non-flow or dead space.

Embodiments of the present disclosure provide a check valve assembly that combines the function of two standard check valves and one Y site component into a single assembly. Typically, known check valves have three components—a fluid entry, a rubber sealing member (disc, diaphragm or umbrella) and a fluid exit. As such, two standard check valves and a Y connector result in seven separate and distinct components. In contrast, certain embodiments of the present disclosure provide a check valve assembly having four components, thereby reducing the total number of individual components (that is, two check valves and one Y connector) to four.

Certain embodiments of the present disclosure provide a dual check valve assembly including one or more deflecting barriers that are configured to prevent flow from the active/open side of the valve peeling open the second diaphragm on the inactive/closed side. The deflecting barrier deflects the fluid flow, but does not cause a significant area of non-flow or dead space.

The check valve assembly may also include guide ribs that are configured to direct fluid flow up around unseated diaphragms. Further, the diaphragms may include raised annular surfaces that increase the contact area between the diaphragms and the valve seats.

On the fluid exit, restraining protuberances, such as circular central upstands, may be used to impart pretension onto the diaphragms but do not excessively disturb the flow through the check valve assembly. Also, the check valve assembly may include support protuberances, such as circular support upstands, that prevent the diaphragms from flexing beyond their elastic limits, but do not excessively disturb fluid flow through the check valve assembly.

Embodiments of the present disclosure provide a check valve assembly that reduces possibility of: micro bubble accumulation, contrast/saline mixing, and back pressure in the line. In contrast, known CT sets include a Y site or similar junction geometry that is susceptible to having areas of restricted flow. Micro bubbles can accumulate in the areas of restricted flow and form a potentially hazardous larger bubble. Embodiments of the present disclosure provide a check valve assembly that replaces such junctions and eliminates, minimizes, or otherwise reduces areas of restricted flow. As such, the chances of micro bubbles accumulating are eliminates, minimized, or otherwise reduced.

Also, the junctions in existing CT sets are also susceptible to allowing droplets of liquid from the inactive line being drawn into the flow from the active line. The mixing of contrast media from one line with saline from the second line can pose problems in trying to complete a CT scan. Embodiments of the present disclosure provide a check valve assembly at the junction, which reduces the possibility of droplets of liquid being drawn from the inactive line.

Integrating the check valve assembly into a CT set lowers back pressure for a given flow rate when compared with traditional CT sets which have two standard check valves and a Y site. As such, there is a lower chance of a pump generating an alarm due to over-pressurization while trying to reach an adequate flow rate for the procedure.

Embodiments of the present disclosure provide a significant cost savings over known systems, as the check valve assembly replaces two externally sourced check valves and a Y connection joint. The check valve assembly also reduces the number of assembly steps involved in the manufacture of the CT sets.

It has been found that the check valve assembly according to embodiments of the present disclosure substantially reduces available fluid for mixing in comparison to prior systems. By joining two fluid lines with the check valve assembly, the likelihood of the two fluids mixing is substantially reduced. Embodiments of the present disclosure provide a check valve assembly that eliminates, minimizes, or otherwise reduces residual fluid volume therein.

As described above, embodiments of the present disclosure provide a check valve assembly that prevents, minimizes, or otherwise reduces the possibility of saline and contrast undesirably mixing. Embodiments of the present disclosure provide a check valve assembly that prevents, minimizes, or otherwise reduces the possibility of image false positives, such as may be caused by spots formed by contrast agent. Overall, embodiments of the present disclosure provide a simpler and more effective check valve assembly in comparison to known systems and methods.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

Variations and modifications of the foregoing are within the scope of the present disclosure. It is understood that the embodiments disclosed and defined herein extend to all alternative combinations of two or more of the individual features mentioned or evident from the text and/or drawings. All of these different combinations constitute various alternative aspects of the present disclosure. The embodiments described herein explain the best modes known for practicing the disclosure and will enable others skilled in the art to utilize the disclosure. The claims are to be construed to include alternative embodiments to the extent permitted by the prior art.

To the extent used in the appended claims, the terms "including" and "in which" are used as the plain-English equivalents of the respective terms "comprising" and "wherein." Moreover, to the extent used in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Various features of the disclosure are set forth in the following claims.

The invention claimed is:

1. A check valve assembly that is configured to couple to a first container that retains a first fluid and a second container that retains a second fluid, the check valve assembly comprising:
a fluid inlet housing including a first fluid inlet port defining a first fluid inlet channel, and a second fluid inlet port defining a second fluid inlet channel;
a fluid outlet housing coupled to the fluid inlet housing, wherein the fluid outlet housing includes a fluid outlet port defining a fluid outlet channel;
a first diaphragm seated over the first fluid inlet channel, wherein at least a portion of the first diaphragm is configured to unseat over the first fluid inlet channel to allow the first fluid to pass from the first fluid inlet channel into the fluid outlet channel; and
a second diaphragm seated over the second fluid inlet channel, wherein at least a portion of the second diaphragm is configured to unseat over the second fluid inlet channel to allow the second fluid to pass from the second fluid inlet channel into the fluid outlet channel,
wherein one or both of the first and second diaphragms comprises an annular edge radially extending from a central hub, wherein the annular edge includes an outer rim that is thicker than the central hub.

2. The check valve assembly of claim 1, further comprising:
a first restraining protuberance that abuts into the first diaphragm; and
a second restraining protuberance that abuts into the second diaphragm.

3. The check valve assembly of claim 1, further comprising:
a first plurality of supporting protuberances that control a range of deflection of the first diaphragm, wherein the first plurality of supporting protuberances block further deflection of the at least a portion of the first diaphragm when the at least a portion of the first diaphragm unseats over the first fluid inlet channel; and
a second plurality of supporting protuberances that control a range of deflection of the second diaphragm, wherein the second plurality of supporting protuberances block further deflection of the at least a portion of the second diaphragm when the at least a portion of the second diaphragm unseats over the second fluid inlet channel.

4. The check valve assembly of claim 1, wherein each of the first and second diaphragms comprises the annular edge radially extending from the central hub.

5. The check valve assembly of claim 1, further comprising one or more walls surrounding a fluid chamber between the first and second fluid inlet channels and the fluid outlet channel.

6. The check valve assembly of claim 5, further comprising a deflecting barrier positioned between openings of the first and second fluid inlet channels.

7. The check valve assembly of claim 5, further comprising one or more guide ribs inwardly extending from the one or more walls, wherein the guide ribs constrain, at least in part, one or both of the first and second diaphragms, and wherein the guide ribs are configured to guide fluid flow from the first and second inlet channels toward the fluid outlet channel.

8. The check valve assembly of claim 7, wherein each of the guide ribs comprises a stem connected to a beveled tip.

9. A fluid delivery system comprising:
a first fluid container that retains a first fluid;
a second fluid container that retains a second fluid; and
a check valve assembly coupled to the first container and the second container, the check valve assembly comprising:
a fluid inlet housing including a first fluid inlet port defining a first fluid inlet channel fluidly connected to the first fluid container, and a second fluid inlet port defining a second fluid inlet channel fluidly connected to the second fluid container;

a fluid outlet housing coupled to the fluid inlet housing, wherein the fluid outlet housing includes a fluid outlet port defining a fluid outlet channel;

a first diaphragm seated over the first fluid inlet channel, wherein at least a portion of the first diaphragm is configured to unseat over the first fluid inlet channel to allow the first fluid to pass from the first fluid inlet channel into the fluid outlet channel; and a second diaphragm seated over the second fluid inlet channel, wherein at least a portion of the second diaphragm is configured to unseat over the second fluid inlet channel to allow the second fluid to pass from the second fluid inlet channel into the fluid outlet channel, wherein one or both of the first and second diaphragms comprises an annular edge radially extending from a central hub, wherein the annular edge includes an outer rim that is thicker than the central hub.

10. The fluid delivery system of claim 9, further comprising a syringe fluidly connected to the fluid outlet port.

11. The fluid delivery system of claim 9, wherein the first fluid container is a contrast container and the first fluid is a contrast agent, and wherein the second fluid container is a saline container and the second fluid is saline.

12. The fluid delivery system of claim 9, further comprising:
a first restraining protuberance that abuts into the first diaphragm; and
a second restraining protuberance that abuts into the second diaphragm.

13. The fluid delivery system of claim 9, further comprising:
a first plurality of supporting protuberances that control a range of deflection of the first diaphragm, wherein the first plurality of supporting protuberances block further deflection of the at least a portion of the first diaphragm when the at least a portion of the first diaphragm unseats over the first fluid inlet channel; and
a second plurality of supporting protuberances that control a range of deflection of the second diaphragm, wherein the second plurality of supporting protuberances block further deflection of the at least a portion of the second diaphragm when the at least a portion of the second diaphragm unseats over the second fluid inlet channel.

14. The fluid delivery system of claim 9, wherein each of the first and second diaphragms comprises the annular edge radially extending from the central hub.

15. The fluid delivery system of claim 9, further comprising one or more walls surrounding a fluid chamber between the first and second fluid inlet channels and the fluid outlet channel.

16. The fluid delivery system of claim 15, further comprising a deflecting barrier positioned between openings of the first and second fluid inlet channels.

17. The fluid delivery system of claim 15, further comprising one or more guide ribs inwardly extending from the one or more walls, wherein the guide ribs constrain, at least in part, one or both of the first and second diaphragms, and wherein the guide ribs are configured to guide fluid flow from the first and second inlet channels toward the fluid outlet channel.

18. The fluid delivery system of claim 17, wherein each of the guide ribs comprises a stem connected to a beveled tip.

19. A check valve assembly that is configured to couple to a contrast container that retains a contrast agent and a saline container that retains saline, the check valve assembly comprising:
a fluid inlet housing including a first fluid inlet port defining a first fluid inlet channel, and a second fluid inlet port defining a second fluid inlet channel;
a fluid outlet housing coupled to the fluid inlet housing, wherein the fluid outlet housing includes a fluid outlet port defining a fluid outlet channel, wherein one or both of the fluid inlet housing and the first outlet housing further comprises one or more walls surrounding a fluid chamber between the first and second fluid inlet channels and the fluid outlet channel;
a first diaphragm seated over the first fluid inlet channel, wherein at least a portion of the first diaphragm is configured to unseat over the first fluid inlet channel to allow the contrast agent to pass from the first fluid inlet channel into the fluid outlet channel, wherein the first diaphragm comprises a first annular edge radially extending from a first central hub, wherein the first annular edge includes a first outer rim that is thicker than the first central hub;
a second diaphragm seated over the second fluid inlet channel, wherein at least a portion of the second diaphragm is configured to unseat over the second fluid inlet channel to allow the saline to pass from the second fluid inlet channel into the fluid outlet channel, wherein the second diaphragm comprises a second annular edge radially extending from a second central hub, wherein the second annular edge includes a second outer rim that is thicker than the second central hub;
one or more guide ribs inwardly extending from the one or more walls, wherein the guide ribs constrain, at least in part, one or both of the first and second diaphragms, and wherein the guide ribs are configured to guide fluid flow from the first and second inlet channels toward the fluid outlet channel;
a deflecting barrier positioned between openings of the first and second fluid inlet channels;
a first restraining protuberance that abuts into the first diaphragm;
a second restraining protuberance that abuts into the second diaphragm;
a first plurality of supporting protuberances that control a range of deflection of the first diaphragm, wherein the first plurality of supporting protuberances block further deflection of the at least a portion of the first diaphragm when the at least a portion of the first diaphragm unseats over the first fluid inlet channel; and
a second plurality of supporting protuberances that control a range of deflection of the second diaphragm, wherein the second plurality of supporting protuberances block further deflection of the at least a portion of the second diaphragm when the at least a portion of the second diaphragm unseats over the second fluid inlet channel.

20. The check valve assembly of claim 19, wherein each of the guide ribs comprises a stem connected to a beveled tip.

* * * * *